United States Patent [19]

Kelly

[11] Patent Number: 4,849,523

[45] Date of Patent: Jul. 18, 1989

[54] PREPARATION OF 2,3,4,6-TETRACHLOROPYRIDINE

[75] Inventor: Jessie Kelly, Oakley, Calif.

[73] Assignee: The Dow Chemical Company, Midland, Mich.

[21] Appl. No.: 92,027

[22] Filed: Sep. 1, 1987

Related U.S. Application Data

[63] Continuation of Ser. No. 817,660, Jan. 10, 1986, abandoned.

[51] Int. Cl.$^4$ ............................................. C07D 213/04
[52] U.S. Cl. ..................................................... 546/345
[58] Field of Search ......................................... 546/345

[56] References Cited

U.S. PATENT DOCUMENTS

| | | | |
|---|---|---|---|
| 3,186,994 | 6/1965 | Johnston | 546/345 |
| 3,334,101 | 8/1967 | Myerly et al. | 546/345 |
| 3,420,833 | 1/1969 | Taplin, III | 260/283 |
| 3,538,100 | 11/1970 | Smith | 260/290 |
| 3,549,647 | 12/1970 | Johnston | 546/345 |
| 3,732,230 | 5/1973 | Brewer et al. | 260/283 R |
| 4,256,894 | 5/1981 | Dietsche et al. | 546/345 |
| 4,517,369 | 5/1985 | Marinak et al. | 546/345 |
| 4,681,945 | 7/1987 | Humphreys et al. | 546/345 |

*Primary Examiner*—Mary C. Lee
*Assistant Examiner*—J. Richter
*Attorney, Agent, or Firm*—Thomas J. Savitsky; D. Wendell Osborne

[57] ABSTRACT

A process for preparing 2,3,4,6-tetrachloropyridine is disclosed which comprises chlorinating 2,6-dichloro-4-trichloromethylpyridine, preferably in the presence of a catalyst, to form 2,3,6-trichloro-4-trichloromethylpyridine which is then reacted with chlorine gas, in the absence of a catalyst, to form the desired product.

9 Claims, No Drawings

PREPARATION OF 2,3,4,6-TETRACHLOROPYRIDINE

This is a continuation of application Ser. No. 817,660, filed Jan. 10, 1986, now abandoned.

BACKGROUND OF THE INVENTION

Preparation of tetrachlorinated pyridines is well known and such compounds are known to be useful as pesticides or as intermediates for the preparation of various pesticides. For example, 2,3,4,6-tetrachloropyridine is useful as a starting material for preparation of certain pesticides (see U.S. Pat. No. 3,549,647). It is recognized in the art that although methods are available for preparing tetrachlorinated pyridines, a major problem is to selectively prepare a substantially pure specific compound. It would be desirable to have a method that results in the production of substantially pure 2,3,4,6-tetrachloropyridine to avoid waste and to facilitate isolation of the desired product.

Many known methods for preparing tetrachlorinated pyridines provide such complex product mixtures and low yields of a specific compound as to render such methods unsuitable as synthetic methods for preparation of a particular compound. However, certain known liquid phase methods are purported to have good selectivity and yields for particular tetrachlorinated pyridine compounds. For example, U.S. Pat. No. 3,186,994 teaches preparation of 2,3,5,6-tetrachloropyridine and 2,3,4,5-tetrachloropyridine; by chlorinating in the absence of a catalyst, an appropriate polychloro-(trichloromethyl)-pyridine reactant in the liquid state at a temperature of at least 160° C., preferably under irradiation with ultraviolet light. U.S. Pat. No. 3,732,230 teaches, inter alia, liquid phase chlorination of an appropriate pyridine hydrochloride to yield a product composition containing 2,3,4,5-tetrachloropyridine and other polychloropyridines. U.S. Pat. No. 4,256,894 teaches, inter alia, preparation, in the presence of a catalyst, of 2,3,5,6-tetrachloropyridine and pentachloropyridine.

None of the above-noted references teach a method for preparing 2,3,4,6-tetrachloropyridine. Such a method is an object of the present invention. Prior art methods which specifically teach preparation of 2,3,4,6-tetrachloropyridine have either described the 2,3,4,6-tetrachloropyridine to be one component of a complex mixture (see U.S. Pat. No. 3,420,833) or have been industrially less desirable methods such as diazotization of 3-amino-2,4,6-trichloropyridine (see J. Den Hertog, et al., *Rec. Trav. Chim.* 69 673, 1950 (Chemical Abstracts 44 8919)).

SUMMARY OF THE INVENTION

The present invention is directed to a process for preparing 2,3,4,6-tetrachloropyridine comprising the steps of:

(a) contacting, in the liquid state, a liquid composition of 2,6-dichloro-4-trichloromethylpyridine with chlorine gas at a temperature of from about 180° C. to about 250° C. to form 2,3,6-trichloro-4-trichloromethylpyridine; and, (b) contacting, in the liquid state and in the absence of a catalyst, a liquid composition of 2,3,6-trichloro-4-trichloromethylpyridine with chlorine gas at a temperature of from about 180° C. to about 250° C., under conditions such that substantially pure 2,3,4,6-tetrachloropyridine is obtained.

Both of the reactions in step (a) and step (b) of the process of the present invention are carried out at atmospheric pressure or superatmospheric pressure, and are preferably conducted under anhydrous conditions. Step (a) is preferably conducted in the presence of a catalyst whereas step (b) is carried out in the absence of a catalyst.

As used herein, 2,6-dichloro-4-trichloromethylpyridine will be referred to as "2,6-Pentagamma"; 2,3,6-trichloro-4-trichloromethylpyridine will be referred to as "2,3,6-Hexagamma"; 2,3,4,6-tetrachloropyridine will be referred to as "2,3,4,6-Tet"; and pentachloropyridine will be referred to as "PCP".

It is contemplated within the scope of the present invention that the process of the invention can be viewed as a multistep process comprising steps (a) and (b) or, alternatively, the present invention can be viewed separately as a process for preparing 2,3,6-Hexagamma (step (a)) and as a process for preparing 2,3,4,6-Tet (step (b)).

DETAILED DESCRIPTION OF THE INVENTION

In carrying out step (a) of the present invention, gaseous chlorine is passed into a liquid 2,6-Pentagamma starting material at a temperature of from about 180° C. to about 250° C. preferably in the presence of a suitable catalyst. A preferred temperature range for the reaction of step (a) is about 190° C. to about 210° C. The 2,6-Pentagamma can be made by procedures known in the art, for example, by using procedures described in U.S. Pat. No. 3,420,833, incorporated herein by reference.

Suitable catalysts which may be employed are those catalysts which catalyze step (a). Examples of suitable catalysts are, for example, Lewis acid type catalysts such as metals, metaloxyhalides or metallic halides capable of being converted to covalent metallic chlorides under the conditions of the chlorination reaction of the present invention, as well as non-metal catalysts, such as, for example, tellurium tetrachloride. While tellurium is a non-metal element, those skilled in the art recognize it possesses properties and characteristics of many metals. Metals themselves such as iron, zinc, aluminum, tantalum, and the like can be employed, preferably in the powdered form. Representative covalent metallic chlorides and/or metallic oxychlorides and/or halides which can be converted to the chloride form include those such as ferric chloride, ferric bromide, aluminum chloride, aluminum bromide, antimony penta-chloride, molybdenum tri- or penta-chloride or oxytetrachloride, tungsten hexachloride, boron trifluoride, titanic chloride, nickel chloride, zinc chloride, tantalum pentachloride, ruthenium trichloride, niobium pentachloride, copper chloride, chromium trichloride, vanadium trichloride, cobalt chloride, and similar materials.

As will be understood by those skilled in the art, no equivalency in activity or operability of the catalyst materials is to be inferred. While certain catalysts have been found to provide good results over a short reaction period, for example, at atmospheric pressure, others which may be operable may require long reaction time periods which may not be economically feasible to obtain similar results. Further, certain catalysts may be superior when employed at elevated temperatures and/or temperatures. The degree of catalytic activity may also vary depending upon the particular product which is to be produced, the degree of catalyst solubility or miscibility with the starting material, the use of fixed bed versus slurried catalysts, etc. In any event, those skilled in the art can, by routine experimentation according to the teachings of the specification and examples herein, readily determine the optimum catalyst and amount thereof required for any particular product to be made or for any particular set of pressure, temperature or time conditions desired.

Catalysts bonded to inert supports or the use of cocatalysts are also contemplated for use in the present invention. Catalysts preferred for use in the present invention include Lewis acid catalysts. Specific preferred catalysts include ruthenium tantalum, tungsten, molybdenum, niobium, aluminum, zinc and iron metals or their halides. Highly preferred catalysts for use in the present invention include the ferric and aluminum halides, and iron and aluminum metals. A preferred catalyst is ferric chloride. A preferred class of catalysts include those which are soluble or readily dispersible in the molten starting material. The catalysts must be employed in an amount effective to catalyze the reaction of step (a), e.g., a catalytic amount, and are usually employed in an amount ranging from about 0.5 to about 20 mole % based on the amount of 2,6-Pentagamma starting material. Preferably, a catalyst concentration of from about 2 to about 3 mole % is employed.

While a catalyst is preferred for the reaction of step (a), surprisingly, no catalyst is required for the reaction of step (b). In addition, and likewise surprising, the reaction of step (b) does not require other conditions, such as irradiation or the use of hydrogen chloride before the addition of chlorine, to proceed satisfactorily.

In carrying out step (b) of the present invention, gaseous chlorine is passed into a liquid 2,3,6-Hexagamma starting material at a temperature of from about 180° C. to about 250° C. A preferred temperature range for the reaction of step (b) is about 200° C. to about 220° C.

It is an advantageous feature of the present invention that step (b) results in the production of substantially pure 2,3,4,6-Tet. That is, other than the 2,3,6-Hexagamma starting material, after a suitable reaction period the reaction mixture contains predominantly 2,3,4,6-Tet. As used herein the phrase "substantially pure" refers to step (b) proceeding in a manner such that the product of step (b), other than unreacted starting material, is composed essentially of the desired 2,3,4,6-Tet in the absence of more than 10 percent other reaction products. It is preferred that step (b) proceed in a manner such that the product of step (b), other than unreacted starting material, is composed essentially of the desired 2,3,4,6-Tet in the absence of more than 5 percent other reaction products, most preferably in the absence of more than 2 percent other reaction products. Other reaction products when present typically include other chlorinated pyridines, for example PCP.

Step (b) typically proceeds in a manner such that the product of step (b) is composed of greater than 45 percent 2,3,4,6-Tet, preferably greater than 60 percent 2,3,4,6-Tet, and most preferably greater than 70 percent 2,3,4,6-Tet.

For both steps (a) and (b), at least an equimolar amount of the chlorine gas reactant is employed with from about 0.5 to about 10 excess molar proportions of chlorine per mole of starting material desirably being employed. The continuous passage of excess chlorine gas through the reaction mixture serves not only to supply a large amount of reactant but to sweep out any carbon tetrachloride or hydrogen chloride by-products. The most suitable rate at which the chlorine gas is fed will vary with the reaction temperature, pressure, reaction mixture volume, etc. An excess amount of from about 0.3 to about 5.0 moles of chlorine per hour is usually employed per mole of the appropriate starting material.

While it is contemplated that the reactions of both step (a) and step (b) will proceed satisfactorily at a superatmospheric pressure, it is not necessary to run either reaction at such a superatmospheric pressure. Therefore, it is another advantageous feature of the present invention that the reactions of both step (a) and step (b) proceed satisfactorily at atmospheric pressure. Therefore, the reactions of step (a) and step (b) are simpler and more cost effective than certain similar processes taught in the prior art. In all embodiments of the present invention, the only constraint placed upon the pressures employed is one of economics and that pressures in excess of atmospheric may be employed.

The reaction process for step (a) is generally illustrated below:

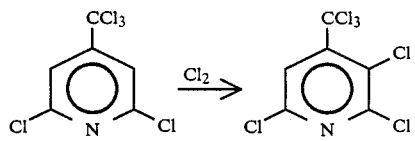

In carrying out step (a), 2,6-Pentagamma in liquid form is usually added to a reactor and, optionally, a catalytic amount of a catalyst is added. The reactor is then heated to about 150° C. and then chlorine gas flow is commenced. The temperature of the reactor is then slowly increased to about 200° C. and the reaction maintained until a sufficient amount of 2,3,6-Hexagamma is obtained. If desired, during the reaction period, the chlorine gas rate and temperature can be increased. Liquid samples from the reactor and vent gases are periodically taken and analyzed by known methods to monitor the course of the reaction. The reaction is terminated by stopping the heating of the reactor and the flow of chlorine thereto and allowing the reactor pressure, if necessary, to drop to atmospheric. Distillation of the reaction product can be performed to obtain the desired 2,3,6-Hexagamma. The 2,3,6-Hexagamma can then be recrystallized and used as a starting material for step (b).

The reaction process for step (b) is generally illustrated below:

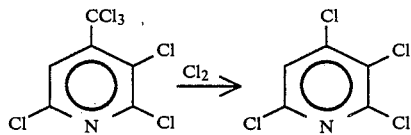

In carrying out step (b), 2,3,6-Hexagamma in liquid form is usually added to a reactor and the reactor then heated to about 220° C. Chlorine gas flow is then commenced and the reaction is allowed to proceed until a sufficient amount of 2,3,4,6-Tet is obtained. Liquid samples from the reactor and vent gases can be periodically taken and analyzed by known methods to monitor the course of the reaction. The reaction is terminated as described for step (a). The desired 2,3,4,6-Tet can be isolated and purified using standard procedures known in the art, for example, by distillation and recrystallization.

If either the reaction of step (a) or step (b) is allowed to run too long, formation of undesired by-products, such as PCP, will result, thus decreasing the yield of the respective desired product. It is readily apparent to one skilled in the art that the respective reactions be run for an amount of time which maximizes the yield of the respective desired product. The optimum respective reaction times will depend on a variety of factors, such as, for example, pressure, temperature, amounts of reactants employed, rate of chlorine feed, and the like. Each operation of the present invention is monitored as described above to determine the optimum reaction time for that particular operation.

The present invention is further illustrated by the following examples; however, these examples should not be interpreted as a limitation upon the scope of the present invention.

EXAMPLE 1

Preparation of 2,3,6-Hexagamma

A reactor was used comprising a three-neck 500 milliliter (ml) flask fitted with: a teflon sparge tube connected via a rotometer and needle valve to a chlorine source; a vent tube connected to a caustic scrubber, and a thermometer. A stirring bar was placed in the flask and a thermowatch controller was attached to the thermometer. The reactor was charged with a melt of 2,6-Pentagamma (99.97% pure) and five percent by weight of a tungsten catalyst. The reaction mixture was heated to between about 175° C. and about 190° C. at atmospheric pressure with stirring, and chlorine was sparged into the solution at the rate of about 60 ml/minute (min). After 27 hours a sample was removed. The sample contained (area percentages) 84% 2,3,6-Hexagamma; 5.3% PCP; 3.4% Heptachloro-gamma-picoline; and 5.5% 2,6-Pentagamma.

EXAMPLE 2

Preparation of 2,3,4,6-Tet

A reactor was used comprising a three-neck 500 ml flask fitted with: a teflon sparge tube connected via a rotometer and needle valve to a chlorine source, a vent tube connected to a caustic scrubber, and a thermometer. A stirring bar was placed in the flask and a thermowatch controller was attached to the thermometer. 2,3,6-Hexagamma (98.85% pure obtained from flash distillation of the product of Example 1) was added to the reactor with the teflon sparge tube about one inch below the surface. The reactor and contents were then heated at atmospheric pressure with stirring using an infrared lamp controlled by the thermowatch controller. When the reactor mixture reached about 175° C., chlorine was sparged into the liquid at a rate of about 60 ml/min. The reaction mixture was then heated to between about 200° C. and 220° C. Samples were removed at 58 and 66 hours. The 58-hour sample contained (area percentages) 30.9% 2,3,4,6-Tet and 2.35% PCP. The 66-hour sample contained (area percentages) 23.7% 2,3,4,6-Tet and 24.2% PCP. The remainder of both samples was substantially the 2,3,6-Hexagamma starting material.

EXAMPLE 3

Preparation of 2,3,6-Hexagamma by Ferric Chloride Catalyzed and Non-Catalyzed Reactions Conjoined Two round bottom 1000 ml flasks were equipped with gas inlet tubes, thermometers, vent lines, and magnetic stirrers. Flask A was charged with 1216 g (4.58 moles) of 2,6-Pentagamma. Flask B with 1213 g (4.57 moles) of 2,6-Pentagamma and 60.5 g (0.37 moles) of ferric chloride catalyst. The vent line from Flask A was connected to Flask B with a trap placed between. Each flask was heated to 150° C. using infrared lamps and thermowatch controllers. Chlorine gas was introduced to Flask A at 60 ml/min. and the temperature was gradually increased to 200° C. in each flask.

After 40 hours the chlorine flow was increased to 81 ml/min. and after 64 hours the temperature was increased to 210° C. in each flask.

At 71 hours flask B was shut down and at 78 hours Flask A was shut down.

At 40 hours the slower rate of reaction in Flask B indicated that the reaction in Flask A was using up the chlorine gas. Increasing the flow caused the reaction to proceed once more at a more rapid rate.

Flask A was sampled at 42 hours at such time the sample contained (area percentage) 15.2% 2,3,6-Hexagamma and was sampled again at 78 hours at such time the sample contained (area percentage) 31.3% 2,3,6-Hexagamma. Flask B was sampled at 64 and 71 hours. The 64 hour sample contained (area percentages) 9.3% PCP and 68.2% 2,3,6-Hexagamma. The 71 hour sample contained 12.3% PCP and 68.3% 2,3,6-Hexagamma.

312 g of 2,3,6-Hexagamma was recovered from Flask A by distillation. 262 g of this was used as a starting material (98.9% pure) in Example 4.

EXAMPLE 4

Preparation of 2,3,4,6-Tet

In a 500 ml round bottom flask equipped with a magnetic stirrer, gas inlet tube, thermometer, and a vent line to a caustic scrubber was placed 262 g (0.87 moles) of 2,3,6-Hexagamma. The flask was heated to 220° C. using an infrared lamp and a Therm-o-watch controller. Chlorine gas was added at 16 ml/min. The reaction was run continuously for 83 hours. At various times during the reaction, samples were taken and analyzed as follows:

| Hours | Area Percent 2,3,6-Hexagamma | Area Percent PCP | Area Percent 2,3,4,6-Tet |
|---|---|---|---|
| 0 | 98.9 | | |
| 18 | 80.8 | | 16.8 |
| 23 | 81.5 | | 18.5 |
| 42 | 67.8 | | 31.65 |
| 46 | 64.7 | | 34.6 |
| 49 | 64.5 | | 34.9 |
| 66 | 64.2 | 0.6 | 35.2 |
| 74 | 50.4 | 1.5 | 48.2 |

After the reaction was terminated, the 2,3,4,6-Tet was separated by distillation and recrystallized using anhydrous ethanol. 59.45 g of crystals, 99.4% pure, were recovered.

EXAMPLE 5

Preparation of 2,3,4,6-Tet

Into a 100 ml three neck flask equipped with a gas inlet tube, thermometer, and a vent line to a caustic scrubber was placed 50 g of 2,3,6-Hexagamma. The flask was heated to 220° C. and controlled at that temperature for the duration of the reaction. Chlorine gas was added and maintained at a flow rate of between about 10 ml/min and 16 ml/min for the duration of the reaction. The reaction was run continuously for 134.5 hours. At various times during the reaction samples were taken and analyzed as follows:

| Hours | Area Percent 2,3,6-Hexagamma | Area Percent PCP | Area Percent 2,3,4,6-Tet | Area Percent 2,6-Pentagamma |
|---|---|---|---|---|
| 0.0 | 97.6 | | | |
| 68.0 | 52.7 | 0.2 | 44.9 | 2.1 |
| 74.0 | 49.2 | 0.2 | 48.3 | 2.1 |
| 83.0 | 45.3 | 0.3 | 52.1 | 1.95 |
| 86.0 | 44.3 | 0.3 | 53.3 | 1.9 |
| 92.5 | 40.7 | 0.4 | 56.7 | 2.0 |
| 99.5 | 36.4 | 0.45 | 60.9 | 2.0 |
| 107.0 | 32.0 | 0.55 | 64.7 | 2.2 |
| 114.5 | 26.9 | 0.6 | 70.1 | 2.15 |
| 122.0 | 23.9 | 0.7 | 72.8 | 2.2 |
| 129.5 | 21.7 | 0.8 | 74.8 | 2.2 |
| 134.5 | 20.1 | 0.9 | 76.2 | 2.25 |

I claim:

1. A process for preparing 2,3,4,6-tetrachloropyridine which comprises contacting, in a liquid state and in the absence of a catalyst, a liquid composition of 2,3,6-trichloro-4-trichloromethylpyridine with at least about 1.5 times the equimolar amount of chlorine gas at a temperature of from about 180° to about 250° C., under conditions such that less than 10 percent of the 2,3,6-trichloro-4-trichloromethylpyridine that reacts is converted to products other than 2,3,4,6-tetrachloropyridine.

2. The process of claim 1 carried out at atmospheric pressure.

3. The process of claim 1 wherein the reaction temperature is from about 200° C. to 220° C.

4. A process of claim 1 under conditions wherein less than 5 percent of the 2,3,6-trichloro-4-trichloromethylpyridine that reacts is converted to products other than 2,3,4,6-tetrachloropyridine.

5. A process of claim 1 under conditions wherein less than 2 percent of the 2,3,6-trichloro-4-trichloromethylpyridine that reacts is converted to products other than 2,3,4,6-tetrachloropyridine.

6. A process of claim 1 wherein 2,3,4,6-tetrachloropyridine comprises at least 45 percent of the total mixture obtained.

7. A process of claim 1 wherein 2,3,4,6-tetrachloropyridine comprises at least 60 percent of the total mixture obtained.

8. A process of claim 1 wherein the 2,3,6-trichloro-4-trichloromethylpyridine employed is obtained by contacting, in the liquid state, a liquid composition of 2,6-dichloro-4-trichloromethylpyridine, optionally containing a Lewis acid catalyst, with chlorine gas at a temperature of from about 180° C. to about 250° C. to form 2,3,6-trichloro-4-trichloromethylpyridine.

9. A process of claim 8 wherein the Lewis acid catalyst is ferric chloride.

* * * * *